United States Patent
Lacombe et al.

(10) Patent No.: US 7,405,174 B2
(45) Date of Patent: Jul. 29, 2008

(54) PROCESS FOR REGENERATION OF A CATALYST THAT CONTAINS AN EUO-STRUCTURAL-TYPE ZEOLITE

(75) Inventors: Sylvie Lacombe, Saint Genis Laval (FR); Julia Magne-Drisch, Vilette de Vienne (FR); Eric Sanchez, Rueil Malmaison (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 295 days.

(21) Appl. No.: 11/216,098

(22) Filed: Sep. 1, 2005

(65) Prior Publication Data
US 2006/0046924 A1 Mar. 2, 2006

(30) Foreign Application Priority Data
Sep. 2, 2004 (FR) .................. 04 09282

(51) Int. Cl.
*B01J 20/34* (2006.01)
(52) U.S. Cl. .............. 502/34; 502/35; 502/37; 502/38; 502/43; 502/49; 502/50; 502/53; 502/54
(58) Field of Classification Search ........... 502/34, 502/35, 37, 38, 43, 49, 50, 53, 54
See application file for complete search history.

(56) References Cited

U.S. PATENT DOCUMENTS

| 4,148,749 A | 4/1979 | Ab der Halden et al. |
| 4,835,139 A | 5/1989 | Tice et al. |
| 5,106,798 A * | 4/1992 | Fung ..................... 502/37 |
| 6,057,486 A | 5/2000 | Merlen et al. |
| 6,133,183 A * | 10/2000 | Capelle et al. ............ 502/37 |
| 6,313,363 B1 | 11/2001 | Joly et al. |
| 2002/0045544 A1 | 4/2002 | Le Peltier et al. |

FOREIGN PATENT DOCUMENTS

JP 58164527 9/1983

OTHER PUBLICATIONS

Patent Abstracts of Japan vol. 007, No. 285 (C-201), Dec. 20, 1983.

\* cited by examiner

*Primary Examiner*—Elizabeth D. Wood
(74) *Attorney, Agent, or Firm*—Millen, White, Zelano, Branigan, P.C.

(57) ABSTRACT

A process for regeneration of a catalyst that comprises at least one EUO-structural-type zeolite in acid form and at least one hydro-dehydrogenating metal, used in a process for isomerization of a hydrocarbon feedstock that comprises aromatic compounds with eight carbon atoms, comprising at least a) a stage for eliminating a majority of the coke, deposited on said catalyst, by combustion in the presence of a gas that contains oxygen at a temperature that is less than or equal to 600° C., and b) a stage for oxychlorination of the product that is obtained from stage a), carried out between 200 and 550° C. in the presence of at least one gas mixture that contains at least oxygen, water and chlorine and/or at least one chlorinated compound, is described.

20 Claims, No Drawings

PROCESS FOR REGENERATION OF A CATALYST THAT CONTAINS AN EUO-STRUCTURAL-TYPE ZEOLITE

This invention relates to a process for regeneration of a catalyst that is based on an EUO-structural-type zeolite, used for the isomerization of hydrocarbon feedstocks that comprise aromatic compounds with eight carbon atoms. The process according to the invention is suitable for regenerating moderately and severely deactivated catalysts.

PRIOR ART

According to the known processes for isomerization of the aromatic compounds with eight carbon atoms (AC8), a feedstock that is generally low in paraxylene relative to the thermodynamic equilibrium of the mixture (i.e., whose paraxylene content is clearly less than that of the mixture with thermodynamic equilibrium at the temperature being considered, whereby this mixture comprises at least one compound that is selected from the group that is formed by metaxylene, orthoxylene, paraxylene and ethylbenzene) and in general high in ethylbenzene relative to this same mixture with the thermodynamic equilibrium is introduced into a reactor that contains at least one catalyst, under suitable temperature and pressure conditions, to obtain a composition, at the outlet of said reactor, made of aromatic compounds with eight carbon atoms that is the closest possible of the composition of said mixture with thermodynamic equilibrium to the temperature of the reactor.

Paraxylene and optionally metaxylene or orthoxylene, which are the desired isomers because they offer a significant advantage in particular for the synthetic fiber industry, are then separated from this mixture.

Much research work has shown that the isomerization of xylenes uses the acid phase of the catalyst, i.e., the zeolite phase, whereas the isomerization of ethylbenzene requires both the use of the acid phase and the hydro-dehydrogenating phase.

The isomerization reactions of aromatic compounds with eight carbon atoms pose several problems that are produced by secondary reactions. Thus, in addition to the primary isomerization reaction, hydrogenation reactions are observed, such as, for example, the hydrogenation of the aromatic compounds into naphthenes, reactions of opening napthenic cycles that lead to the formation of paraffins that have at most the same number of carbon atoms per molecule as the napthenes from which they are obtained. Also observed are cracking reactions, such as, for example, the cracking of paraffins that lead to the formation of light paraffins that typically have 3 to 5 carbon atoms, reactions of dismutation and transalkylation that lead to the formation of benzene, toluene, aromatic compounds with 9 carbon atoms and heavier aromatic compounds. All of these secondary reactions strongly penalize the yields of desired products and depend on the catalyst that is used for the isomerization reaction of aromatic compounds with eight carbon atoms. In addition to these secondary reactions, it is well known to one skilled in the art that, despite the presence of a metal phase on the catalyst and high hydrogen pressure during the reaction, the catalyst is gradually deactivated by coke formation.

The effectiveness of the catalyst and its stability over time depend in particular on the good dispersion of the metal element or elements of the catalyst. It thus is desirable to have the highest dispersion possible of the metal, such that a maximum number of metal atoms is accessible to the reagents. The size of the metal particles should be small, preferably less than or equal to 2 nm, and their distribution on the catalyst should be the most homogeneous possible, on the one hand on the freshly prepared catalyst (i.e., the catalyst that has not been brought into contact with hydrocarbons under isomerization conditions) and, on the other hand and primarily, after the regeneration of the catalyst that is at least partially deactivated.

The standard regeneration of the catalyst comprises a stage during which the coke is removed by combustion. In this stage, the catalyst is heated in a more or less dilute oxygen stream at a temperature from about 400 to 600° C. so as to burn the coke. If particular precautions are not taken during this treatment, a more or less significant agglomeration of the platinum particles occurs, i.e., a more or less significant loss of surface area of the metal particles. The platinum atoms become less accessible, which produces a more or less significant loss of activity for the catalyst. This sintering phenomenon is well known to one skilled in the art. This is why special regeneration procedures have been developed.

In the case of catalysts that are used in the reforming process and in particular in the case of standard reforming catalysts based on alumina and at least one metal of group VIII of the periodic table, the method for regeneration by combustion followed by oxychlorination was broadly studied.

Patent Application WO94/05419 teaches that it is more difficult to perform this oxychlorination stage on a reforming catalyst that is based on zeolite and a metal of group VIII and discloses a procedure for regeneration that comprises, i.a., a combustion stage and a temperature treatment stage in the presence of water, a chlorine source, an oxygen source and a cover gas source on a catalyst that is based on zeolite and a metal of group VIII. Patent Application WO98/47615 describes a method for regeneration of a reforming catalyst that contains an L-structural-type zeolite, a metal of group VIII and a halogen element, for example chlorine, whereby the regeneration method consists of oxychlorination, followed by purging for removing excess chlorine, itself followed by a reduction. The zeolite is obtained by hydrothermal synthesis of a synthesis mixture that contains water, a potassium source, an aluminum source, a silica source and a divalent cation source that is selected from the group that comprises magnesium, calcium, barium, manganese, chromium, cobalt, nickel and zinc. The zeolite that is obtained is in basic form, for example in KMgL form. The zeolites that are present in the reforming catalysts that are disclosed in these patent applications are in basic form, which makes them much less sensitive to dealuminification risks in the presence of chlorine at high temperature.

A procedure for rejuvenation of a catalyst that is based on an acid zeolite, for example a ZSM-3, ZSM-4 or ZSM-18 zeolite, and a noble metal is disclosed in U.S. Pat. No. 4,645, 751. This procedure consists in reducing the catalyst under hydrogen, in treating it then under a cover gas that contains HCl, then in optionally performing a second reduction.

DESCRIPTION OF THE INVENTION

This invention has as its object a process for regeneration of a catalyst that comprises at least one EUO-structural-type zeolite in acid form and at least one hydro-dehydrogenating metal, whereby said catalyst is used in a process for isomerization of a hydrocarbon feedstock that comprises aromatic compounds with eight carbon atoms. The regeneration process according to the invention comprises at least:

a) a stage for eliminating a majority of the coke, deposited on said catalyst, by combustion in the presence of a gas that contains oxygen at a temperature that is less than or equal to 600° C., and b) a stage for oxychlorination of the product that is obtained from stage a), carried out between 200 and 550° C., in the presence of at least one gas mixture that contains at least oxygen, water and chlorine and/or at least one chlorinated compound.

The catalyst that comprises at least one EUO-structural-type zeolite in acid form and at least one hydro-dehydrogenating metal is regenerated by use of the process according to the invention when it has lost at least a portion of its initial activity. The loss of activity of the catalyst is linked to the presence of coke that inevitably forms during the isomerization reaction, during which the hydrocarbon feedstock that comprises the aromatic compounds with eight carbon atoms is brought into contact with said catalyst, and it is deposited on said catalyst that contributes to a reduction of overall catalytic performances. Said hydrocarbon feedstock contains at least ethylbenzene and a mixture of xylene isomers.

The catalyst that comprises at least one EUO-structural-type zeolite in acid form and at least one hydro-dehydrogenating metal is regenerated according to the process of the invention when its activity, under the conditions initially selected for the reaction for isomerization of aromatic compounds, represents no more than 50 to 90% of the initial activity in terms of ethylbenzene conversion, and preferably no more than 50 to 85% of the initial activity for ethylbenzene conversion.

In terms of this invention, the activity of the catalyst corresponds to the conversion into ethylbenzene. According to the definition that is well known to one skilled in the art, conversion into ethylbenzene is defined as follows: conversion into ethylbenzene=[(quantity of ethylbenzene in the hydrocarbon feedstock−quantity of ethylbenzene at the outlet of the isomerization reactor)/quantity of ethylbenzene in the hydrocarbon feedstock]. The initial activity in terms of the conversion of ethylbenzene corresponds to the conversion into ethylbenzene at the end of 168 hours of reaction. According to the industrial conditions of the site where the isomerization process is carried out, one skilled in the art is able to decide at what time the regeneration of the catalyst is most suitable. It is usually desirable, for economic reasons, to regenerate the catalyst before its activity becomes too weak, i.e., before it is less than 50% of the initial activity in terms of ethylbenzene conversion.

The catalyst that is subjected to the regeneration process according to the invention regains virtually, and even entirely, its initial activity.

The cycle that comprises a regeneration period and an isomerization period can be repeated several times on the same catalyst.

The catalyst that is used in the regeneration process of this invention comprises at least one EUO-structural-type zeolite, i.e., an EU-1, TPZ-3 or ZSM-50 zeolite; it is preferably an EU-1 zeolite.

The EUO-structural-type EU-1 zeolite, already known in the prior art, exhibits a monodimensional microporous network, whose pore diameter is 4.1×5.7 Å (1 Å=1 angstrom=1.10-10$^m$) ("Atlas of Zeolites Structure Types," W. M. Meier and D. H. Olson, 4$^{th}$ Edition, 1996). In contrast, N. A. Briscoe et al. taught in an article of the journal Zeolites (1988, 8, 74) that these monodimensional channels have side pockets with a depth of 8.1 Å and a diameter of 6.8×5.8 Å. The synthesis mode of the EU-1 zeolite and-its physico-chemical characteristics were described in Patent EP-B1-42 226. The ZSM-50 zeolite is described in U.S. Pat. No. 4,640,829, and the TPZ-3 zeolite is described in Patent Application EP-A1-51 318.

The EUO-structural-type zeolite, preferably the EU-1 zeolite, present in the catalyst that is used in the regeneration process of this invention, comprises silicon and at least one T element that is selected from the group that is formed by aluminum, iron, gallium and boron, preferably aluminum, with an overall Si/T atomic ratio of more than 5.

The EUO-structural-type zeolite, preferably the EU-1 zeolite, is at least partially, preferably virtually totally, in acid form, i.e., in the form of hydrogen ($H^+$), whereby the sodium content is preferably such that the Na/T ratio is less than 0.5, preferably less than 0.1, even more preferably less than 0.02.

According to a preferred embodiment of the catalyst that is used in the regeneration process of this invention, the EUO-structural-type zeolite, preferably the EU-1 zeolite that it comprises, has a crystal size that is less than 5 micrometers (μm). The size of crystallites is usually more than 0.001 μm and often more than 0.01 μm. These crystals or crystallites are often combined into aggregates that have a grain size such that the value of Dv,90 is less than or equal to 500 μm, often less than 400 μm, and most often less than 200 μm. An aggregate is a unit that is formed by at least two zeolite crystals that have at least one contact point between them. The size of the aggregates is determined by laser-diffraction granulometry. This measurement is carried out on the zeolite powder that is suspended in water. After a first measurement, the suspension is subjected to ultrasound for thirty seconds, and then a new measurement is carried out. The ultrasound that is used is characterized by a power of 50 W and a frequency of 50 kHz. This procedure is repeated until the result no longer varies (at ±5%). The size distribution of the aggregates that is defined by volume is calculated from light signals collected by detectors and with the Fraunhofer theory. Dv,X is defined as being the diameter of the equivalent sphere such that X % by volume of aggregates has a size that is smaller than said diameter, after ultrasound. These characteristics will be obtained directly during the synthesis of the zeolite and/or by any method that makes it possible to reduce the size of the aggregates, such as, for example, the post-synthesis grinding or else a suitable mixing before shaping.

The catalyst also comprises at least one matrix. Said matrix comprises at least one compound that is selected from the group that is formed by clays, magnesia, aluminas, silicas, silica-aluminas, titanium oxide, boron oxide, zirconia, aluminum phosphates, titanium phosphates and zirconium phosphates. The matrix is preferably alumina.

The catalyst that is used in the regeneration process according to this invention also comprises at least one hydro-dehydrogenating element of the periodic table, preferably selected from among the metals of groups VB, VIB, VIIB and VIII. The hydro-dehydrogenating element is preferably selected from among palladium, platinum, nickel, iron, cobalt, chromium, manganese, tungsten, vanadium, and molybdenum. Very preferably, the hydro-dehydrogenating element is a metal of group VIII, advantageously platinum or palladium. Said catalyst, in addition to the hydro-dehydrogenating element, can also contain at least one metal that is selected from among the metals of groups IIIA and IVA, preferably selected from among indium and tin. It can also contain sulfur.

More particularly, the catalyst, regenerated according to the process of the invention, comprises by weight relative to the total mass of the catalyst:

1 to 90% by weight of at least one EUO-structural-type zeolite, preferably 3 to 60% by weight, and even more preferably 4 to 40% by weight, 0.01 to 2% by weight of at least one hydro-dehydrogenating metal, preferably 0.05 to 1% by weight, optionally 0.01 to 2% by weight of at least one additional element that is selected from groups IIIA and IVA of the periodic table, preferably 0.05 to 1% by weight, optionally sulfur, and a binder that ensures the addition by weight to 100% of the catalyst.

The new, freshly prepared catalyst that has not yet been subjected to the isomerization reaction preferably exhibits a dispersion of hydro-dehydrogenating metal of between 75 and 100%, and more preferably between 80 and 100%. The dispersion of hydro-dehydrogenating metal is determined by $H_2$—$O_2$ titration according to a method that is well known to one skilled in the art. The catalyst is preferably shaped in the form of balls or extrudates. Said new catalyst optionally can contain a small quantity of halogen, preferably chlorine, preferably between 1000 and 5000 ppm by weight relative to the total mass of the catalyst. Very preferably, said catalyst does not contain halogen; preferably it is devoid of chlorine.

A method for preparation of the catalyst is given in U.S. Pat. No. 6,057,487 as well as in Patent Application EP-A-0, 923,987. To prepare said catalyst, first a treatment of the EUO-structural-type zeolite, for example the EU-1 zeolite, raw straight from synthesis, is performed according to any method that is known to one skilled in the art; for example, a calcination stage is initiated under a dry air flow, whose purpose is to eliminate the organic structuring that is occluded in the micropores of the zeolite, then at least one ion exchange stage is initiated by, for example, at least one $NH_4NO_3$ solution so as to eliminate at least partly, preferably virtually entirely, any alkaline cation, in particular sodium, that is present in cationic position in the zeolite. The preparation of the catalyst is continued by mixing the matrix and the zeolite that are prepared above, then it is shaped. The shaping of the catalyst according to the invention is generally such that the catalyst is preferably in extrudate or ball form, for the purpose of its use.

The conditions of shaping the zeolite, the selection of the matrix, optionally the preliminary grinding of the zeolite, the peptization process, the addition of pore-forming agents, the mixing time, the extrusion pressure if the catalyst is put in extrudate form, the speed and time of drying are determined for each matrix according to the rules that are well known to one skilled in the art so as to obtain a catalyst that is preferably in extrudate or ball form. The preparation of the catalyst is generally continued by calcination, usually at a temperature of between 250° C. and 600° C., inclusive, preferably preceded by a drying, for example in an oven, at a temperature that is generally between the ambient temperature and 250° C., inclusive, preferably between 40° C. and 200° C., inclusive. Said drying stage is preferably conducted during the rise in temperature that is necessary for carrying out said calcination. The shaping of the EUO-structural-type zeolite, for example the EU-1 zeolite, can be carried out on the crude synthesis zeolite, i.e., containing the organic structure and alkaline cations, generally sodium. In this case, the calcination stage under a stream of dry air, whose purpose is to eliminate the organic structuring, and ion exchange stages by at least one $NH_4NO_3$ solution are carried out on the shaped catalyst that comprises the zeolite and the matrix. The catalyst obtained after said calcination is put into ball or extrudate form. The deposition of at least one element of group VIII of the periodic table and optionally at least one element that is selected from the unit that is formed by groups IIIA and IVA of the periodic table can be carried out at any time of the preparation, either before the shaping, or during the mixing of the zeolite and the matrix, whereby the zeolite is mixed with the unit that consists of the precursor(s) of said element(s) and the matrix, or, preferably, after the shaping. The deposition of at least the hydro-dehydrogenating element is generally carried out by the dry impregnation technique, the excess impregnation technique, or preferably by ion exchange(s). In the case of the ion exchange from metal precursors of group VIII, for example platinum and/or palladium, platinum and/or palladium salts such as hexachloroplatinic acid and/or hexachloropalladic acid are usually used with or without the presence of competing agents, such as, for example, hydrochloric acid. In the case where at least one other metal that is selected from the unit that is formed by groups IIIA and IVA of the periodic table is also introduced, all the deposition techniques that are known to one skilled in the art and all the precursors are suitable for the introduction of additional metal.

This catalyst is used in the process for isomerization of a hydrocarbon feedstock that comprises aromatic compounds with eight carbon atoms, in particular ethylbenzene and a mixture of isomers of xylene. It is preferred to use a catalyst that has a hydro-dehydrogenating metal distribution that is close to 100% so as to ensure the most homogeneous distribution of metal crystallites possible and to optimize the quantity of accessible metal sites. The distribution of the metal crystallites depends in particular on the quantity of prepared catalyst, and the good monitoring of preparation parameters such as, for example, the temperature. In the case where the dispersion of the hydro-dehydrogenating metal is less than 100%, for example less than 90%, it is possible to obtain a catalyst that has a better dispersion of metal particles by subjecting this solid to an oxychlorination treatment under the conditions defined below. The sizes of metal crystallites were measured with a high-resolution electronic microscope. The catalyst that is intended to be observed by transmission electron microscopy is ground in an agate mortar then suspended in ethanol by ultrasound. A drop of this suspension is then deposited on a copper grid that is covered by a thin holey carbon film. After being dried briefly, the sample is observed by the so-called clear field technique. The size of the metal crystallites, observed on the solid that is obtained by the process described above, is less than or equal to 2 nm.

The stage for eliminating coke according to the first stage a) of the regeneration process according to the invention is preferably carried out on a catalyst that contains virtually no water, generally less than 2% by weight of catalyst. If the catalyst, at least partially deactivated, that it is desired to regenerate is obtained from a storage zone, it is preferable, before carrying out the combustion of coke by the oxygen, to heat the catalyst under cover gas at a temperature of about 150° C. for an adequate period to duly eliminate the water before raising the temperature during the combustion stage of the coke. This drying makes it possible to prevent dealuminification of the EUO-structural-type zeolite, which could occur during the combustion of the coke when the catalyst contains water.

The first stage of the process according to the invention that consists in eliminating the majority of the coke that is deposited on the catalyst is carried out by bringing the catalyst, previously used for isomerizing a hydrocarbon fraction that comprises aromatic compounds with eight carbon atoms, into contact with a gas that contains oxygen by gradually increasing the temperature until the exothermal reaction of combustion or coke burning, usually between 300 and 600° C., is observed. This combustion is carried out carefully, and the operating conditions are adjusted such that preferably the temperature does not exceed 550° C. and more preferably does not exceed 500° C. During this combustion, the majority of the coke is burned such that the content by weight of residual coke on the catalyst after combustion is generally less than 20% and preferably less than about 10% of the content by weight of coke of the catalyst before combustion. The gas that contains the oxygen that is used in stage a) of the process according to the invention is generally a mixture of oxygen and cover gas, usually containing 0.1 to 20% by volume of oxygen, preferably 0.2 to 10% by volume of oxygen. This can be, for example, air or air diluted by a cover gas. The proportion of oxygen in the gas that is used for the elimination of coke by combustion can also be variable based on the evolution of the exothermal combustion reaction.

After the burning of the coke, the catalyst is put under cover gas and subjected to the second stage of the regeneration process according to the invention, optionally after having adjusted its temperature to, for example, the desired value for oxychlorination. It is also possible to cool the catalyst, after the coke is burned, to the ambient temperature and to keep it under cover gas at this temperature, before subjecting it to oxychlorination. This will be the case, for example, if the burning of the coke and the oxychlorination are not carried out on the same site.

According to stage b) of the process according to the invention, the oxychlorination stage comprises bringing the catalyst that is treated according to stage a) into contact with chlorine and/or at least one chlorinated compound in the presence of a gas that contains oxygen at a temperature from about 200 to 550° C., and preferably from about 300 to 550° C., even more preferably from about 400 to 500° C. Preferably, said catalyst that is obtained from stage a) is first brought into contact with the gas that contains oxygen then with the chlorine and/or the chlorinated compound. The chlorine and/or the chlorinated compound is used in a quantity that represents in all 0.5 to 10% by weight calculated by weight of chlorine relative to the weight of the catalyst that is used for carrying out stage a), and preferably 1 to 5% by weight. The chlorinated compound can be a mineral or organic chlorinated compound. When a chlorinated organic compound is used, it is usually preferred to use a chloroalkane. The oxychlorination stage according to the process of the invention is carried out in the presence of water that is introduced either in the form of water vapor, with the gas containing oxygen, or at the time of introduction of the chlorine and/or at least one chlorinated compound.

The oxychlorination stage of the catalyst according to the process of the invention can be carried out "off site" or "ex situ," or else "on site" or "in situ." "In-situ" treatment is defined as treatment that is carried out in the zone or zones in which the actual isomerization reaction itself will be carried out or in a zone or zones in direct or indirect communication with said isomerization zone. "Ex-situ" treatment is defined as treatment that is carried out either close to the site of the industrial unit for isomerization, in a zone that is not in the immediate vicinity of the isomerization zone, or at a greater or lesser distance geographically from the industrial unit.

The oxychlorination stage according to the process of the invention consists in heating the catalyst that is obtained from stage a) in the presence of a gas stream that contains oxygen, whereby the content by weight of oxygen of the gas mixture is preferably 10 to 50% by weight, and preferably 15 to 35% by weight. Heating in the presence of the gas that contains oxygen is generally carried out gradually up to the temperature selected for bringing the catalyst into contact with chlorine and/or at least one chlorinated compound. The temperature increases by, for example, about 5° C. per minute up to said selected temperature. Then, chlorine ($Cl_2$) and/or at least one chlorinated compound is introduced into the gas stream of oxygen, kept at the selected temperature. It is possible to use a mineral chlorinated compound, for example hydrochloric acid (HCl) and/or an organic chlorinated compound, preferably a chloroalkane such as carbon tetrachloride, dichloropropane, dichloroethane or chloroform.

The oxychlorination stage according to the process of the invention is carried out in the presence of water. The water can be introduced, in the form of water vapor, with the gas that contains oxygen, whereby the content by weight of water of the gas mixture is advantageously between 0.01 and 5% by weight, very advantageously between 0.02 and 2% by weight and even more advantageously between 0.02 and 1% by weight. It is possible to use, for example, moist air. Water can also be introduced at the time when chlorine and/or at least one chlorinated compound is introduced, once the catalyst that is obtained from stage a) has been brought into contact with a gas stream that contains oxygen and once the temperature that is selected for bringing the catalyst into contact with chlorine and/or at least one chlorinated compound is reached.

The quantity of chlorine and/or chlorinated compound that is injected preferably represents 0.5 to 10% by weight, very preferably 1 to 5% by weight, of chlorine relative to the weight of the catalyst that is used to carry out stage a). The injection flow rate of the chlorine and/or the chlorinated compound is usually calculated such that the necessary duration of the injection of the selected quantity of chlorine is about 0.5 to 24 hours and preferably one hour to three hours. When the introduction of chlorine and/or that of the chlorinated compound has ended, the catalyst is then cooled, in the presence of a gas stream that contains oxygen and optionally water vapor, as described above, generally up to the ambient temperature.

The residual chlorine content on the catalyst usually does not exceed about 30 to 50% by weight of the mass of injected chlorine.

The dispersion of the metal particles on the catalyst that is obtained after oxychlorination is between 75 and 100%, preferably between 80 and 100% and very preferably more than 90%.

The oxychlorination stage is generally carried out after the stage of elimination of coke by combustion. Although it is also possible to carry out the combustion and oxychlorination simultaneously, it is generally preferred to carry out first the combustion of the coke, then the oxychlorination.

The regenerated catalyst that is obtained at the end of stage b) of the process according to the invention is subjected to a reduction before being brought into contact again with the hydrocarbon feedstock under the isomerization conditions provided below in this description. The reduction is generally carried out with the help of a gas that contains at least one reducing compound, preferably hydrogen, which preferably exhibits a purity that is higher than 90% in mols. The reduction is advantageously carried out in stages up to a temperature of 300 to 700° C., preferably 400 to 600° C., and very preferably 400 to 520° C., for an adequate period so that the concentrations of reducing compounds are the same at the inlet and at the outlet of the reactor. The duration of the reduction stage is preferably from about 1 to 40 hours, and preferably from about 1 to 8 hours. The total pressure is between atmospheric pressure and 3 MPa, and preferably it is from about 1 to 2 MPa. The hydrogen flow rate (addition of fresh hydrogen and recycled hydrogen from the outlet to the inlet of the reactor) is from about 0.1 l/h/g to 100 l/h/g of catalyst. This reduction stage is preferably carried out "in situ."

The hydrocarbon feedstock that is used in the isomerization process, in which the catalyst that is based on the EUO-structural-type zeolite is used, comprises aromatic compounds with eight carbon atoms including ethylbenzene and a mixture of xylenes. The isomerization process is conducted according to any method that is known to one skilled in the art. For example, the temperature of the isomerization reaction is from 300° C. to 420° C., preferably from 320° C. to 400° C., and even more preferably from 350° C. to 400° C.; the partial hydrogen pressure is from 0.3 to 1.5 MPa, preferably 0.4 to 1.2 MPa; the total pressure is from 0.45 to 1.9 MPa, preferably 0.6 to 1.5 MPa, the PPH (weight of feedstock/weight of catalyst/hour) is from 0.25 to 15 $h^{-1}$, preferably 1 to 10 $h^{-1}$, and even more preferably 2 to 6 $h^{-1}$.

According to a preferred embodiment of the isomerization process according to this invention, at least one compound that has a boiling point of between 80° C. and 135° C. and more particularly at least one compound that is selected from the group that is formed by the paraffins with eight carbon atoms per molecule, benzene, toluene, napthenes with eight carbon atoms, is introduced with the feedstock that is to be isomerized and with the hydrogen that is necessary to the reaction. This or these compound(s) is (are) added to the feedstock that is to be isomerized in recycling form, in the form of fresh compounds or in the form of a mixture of recycled compounds and fresh compounds in quantities such that the mass percentages of compounds that are added relative to the total feedstock that enters into the reactor are usually as follows:

The mass percentage of paraffins with eight carbon atoms, in the possible case where it is added to the feedstock, is from about 0.1% to 10%, preferably from about 02. to 2%, The mass percentage of naphthenes with eight carbon atoms, in the possible case where it is added to the feedstock, is from about 0.5% to 15%, and preferably from about 2% to 8%, The mass percentage of toluene, in the possible case where it is added to the feedstock, is from about 0.1% to 10%, preferably from about 0.2% to 5%, The mass percentage of benzene, in the possible case where it is added to the feedstock, is from about 0.1% to 10%, preferably from about 0.2% to 2%.

The mass percentage of total added compounds, when several compounds are added, usually represents about 0.1% to 20% by mass and preferably about 2% to 15% by mass relative to the total feedstock that is part of the isomerization zone.

In an embodiment of the invention, the catalyst that is used in the isomerization process is subjected to a sulfurization treatment before it is brought into contact with the hydrocarbon feedstock that is to be isomerized and that comprises aromatic compounds with eight carbon atoms. The sulfurization of the catalyst is then carried out by means of a sulfur compound, for example the hydrogen sulfide or a hydrogen sulfide precursor. It is carried out, except for feedstock, either before introducing said catalyst into the reactor where the isomerization reaction occurs, or when said catalyst is already in place in the reactor. In general, before sulfurization, the hydro-dehydrogenating metal compound that is contained in the catalyst is reduced. This sulfurization stage can be carried out by pure hydrogen sulfide or by a preferably organic hydrogen sulfide precursor that will then be decomposed in the reactor. Without this list exhibiting a limiting nature, the sulfur-containing organic compounds that can be used in the sulfurization stage are, for example, the alkyl sulfide compounds, the aryl sulfide compounds, and the alkylaryl sulfide compounds. By way of example, butyl ethyl sulfide, diallyl sulfide, dibutyl sulfide, dipropyl sulfide, dimethyl disulfide (DMDS), thiophene, dimethyl thiophene and ethylthiophene will be cited. The sulfurization stage of the catalyst is usually carried out under a neutral or reducing atmosphere at a temperature from about 20° C. to 500° C. and preferably from about 200° C. to 400° C., at an absolute pressure of about 0.1 to 5 MPa, and preferably from about 0.3 to 3 MPa, and with a (cover or reducing) gas volume per volume of catalyst per hour (V.V.H.) of about 50 $h^{-1}$ to 600 $h^{-1}$ and preferably of about 100 $h^{-1}$ to 200 $h.^{-1}$. Most often, the cover gas that is used is nitrogen, and the reducing gas is usually hydrogen, most often essentially pure.

In another embodiment of the invention, the catalyst that is used in the isomerization process is subjected to passivation with ammonia before the beginning of the isomerization reaction of the hydrocarbon feedstock that comprises aromatic compounds with eight carbon atoms. The passivation with ammonia is carried out most often in two periods: an injection of ammonia, in $NH_3$ vapor form, or in the form of at least one precursor compound of ammonia, then a continuous injection of ammonia in $NH_3$ vapor form or in the form of at least one precursor compound of the ammonia during the introduction of the feedstock that is to be isomerized. The duration of second-time injection of ammonia in $NH_3$ vapor form or of the ammonia precursor depends on how long it takes to bring the catalyst to nominal conditions; in particular it depends on the stabilization of temperatures within the catalyst. The first injection is preferably carried out with $NH_3$ in vapor form, and the second injection is carried out with at least one precursor compound of ammonia. The precursors of ammonia ($NH_3$) that can be used within the framework of this invention are all compounds that are known to one skilled in the art that, in the presence of hydrogen, decompose into ammonia that is fixed to the catalyst. Among the compounds that can be used, it is possible to cite the aliphatic amines, such as, for example, n-butylamine.

In another embodiment of the invention, the catalyst that is based on at least one EUO-structural-type zeolite is subjected, before the beginning of the isomerization reaction, to sulfurization treatment and to the passivation in the presence of ammonia ($NH_3$). The passivation can be carried out before or after the sulfurization stage. The sulfurization stage is preferably carried out before the passivation stage. These two sulfurization and passivation stages can be carried out before or after the introduction of the catalyst into the isomerization reactor. In a preferred way, the passivation stage in the presence of ammonia is carried out whereas the catalyst is already in place in the isomerization reactor.

In another embodiment of the invention, the catalyst that comprises at least one EUO-structural-type zeolite in acid form is subjected, before being used in the isomerization process of said hydrocarbon feedstock that comprises aromatic compounds with eight carbon atoms, to an oxychlorination pretreatment, which, carried out in combination with the regeneration according to the invention, makes it possible to lead to better performance levels of the isomerization process, in particular in terms of activity, than when the catalyst is not subjected to this pretreatment. This pretreatment comprises bringing the catalyst into contact with chlorine and/or at least one chlorinated compound in the presence of a gas that contains oxygen at a temperature of about 200 to 550° C., preferably of about 300 to 550° C., and even more preferably of about 400 to 500° C. Said catalyst is preferably first brought into contact with the gas that contains oxygen, then with chlorine and/or the chlorinated compound. The chlorine and/or the chlorinated compound is used in a quantity that represents in all 0.5 to 10% by weight calculated by weight of chlorine relative to the catalyst weight, and preferably 1 to 5% by weight. The oxychlorination pretreatment according to the process of the invention is carried out in the presence of water that is introduced either in the form of water vapor, with the gas that contains oxygen, or at the time of introduction of chlorine and/or at least one chlorinated compound.

According to the invention, prior to the isomerization reaction of the hydrocarbon feedstock that comprises aromatic compounds with eight carbon atoms, it is possible to operate, in addition to the sulfurization of the catalyst, and in addition to the passivation of the catalyst in the presence of ammonia, an activation stage of the catalyst, in the presence of an aromatic hydrocarbon feedstock with eight carbon atoms, by using at least one parameter that is selected from among the pressure and the temperature at a value such that a catalyst is obtained that comprises carbon. For this purpose, said activation is carried out under strict temperature and pressure conditions. Thus, for example, activation at a temperature of between 400° C. and 500° C., and preferably at a temperature of between 420° C. and 450° C., is carried out. It is also possible to vary the pressure. For example, a total pressure of between 1 and 2 MPa, and preferably between 1.2 and 1.8 MPa, is applied. The process for activation of the catalyst is carried out in the same reaction zone as the reaction for isomerization of xylenes and ethylbenzene.

EXAMPLE

This example illustrates the regeneration of a catalyst that comprises an EU-1 zeolite that has undergone deactivation by being brought into contact with hydrocarbons for 1464 hours.

The raw material that is used is an EU-1 zeolite, raw straight from synthesis, that comprises the organic structure, i.e., hexamethonium bromide, silicon and aluminum, and that has an overall Si/Al atomic ratio that is equal to 13.2, a content by weight of sodium relative to the dry EU-1 zeolite weight of about 1.6%.

This EU-1 zeolite first undergoes a so-called dry calcination at 550° C. under a flow of air for 6 hours. Then, the solid that is obtained is subjected to three ion exchanges in a 10N $NH_4NO_3$ solution, at about 100° C. for 4 hours for each exchange.

At the end of these treatments, the EU-1 zeolite in $NH_4$ form has an overall Si/Al atomic ratio that is equal to 18.1, a content by weight of sodium relative to the weight of the dry EU-1 zeolite of 50 ppm, a specific surface area that is measured by the BET method of 410 $m^2/g$ and a pore volume, with nitrogen, that is measured at −196° C. and at P/PO=0.15, with 0.16 $cm^3$ of liquid nitrogen per gram. In the EU-1 zeolite, 100% of the aluminum atoms are in a tetrahedral coordination number according to NMR analysis of aluminum 27.

The EU-1 zeolite is then shaped by extrusion with an alumina gel so as to obtain, after drying and calcination under dry air, the substrate S1 that consists of extrudates of 1.4 mm of diameter, which contains 10% by weight of the EU-1 zeolite in H form and 90% alumina. The diameter of the pores of the thus prepared catalyst, measured by mercury porosimetry, is between 40 and 90 Å, whereby the distribution of the diameters of these mesopores is monomodal and centered on 70 Å.

The thus obtained S1 substrate is subjected to an anion exchange with hexachloroplatinic acid in the presence of a competing agent (hydrochloric acid), so as to introduce 0.3% by weight of platinum relative to the catalyst. The moist solid is then dried at 120° C. for 12 hours and calcined under a flow of dry air at the temperature of 500° C. for one hour.

The thus obtained catalyst contains 10.0% by weight of EU-1 zeolite in H form, 89.7% of alumina and 0.29% of platinum. For the metal phase, it exhibits a dispersion of 96%, determined by $H_2$—$O_2$ titration.

A reactor is loaded with 60 g of said EUO zeolite-based catalyst.

This catalyst, after reduction to 480° C. under hydrogen, undergoes a sulfurization stage. A quantity of $H_2S$ that is equal to 0.1% by weight relative to the catalyst is introduced. After injection of $H_2S$, the reactor is left for 1 hour at 380° C. with hydrogen recycling and without an addition of hydrogen. Then, the temperature of the reactor is increased to 390° C. in 1 hour. It then remains for 2 hours at 390° C.

The feedstock that is to be isomerized is a mixture of aromatic compounds with 8 carbon atoms and compounds that have boiling points of between 80 and 135° C. that are added via recycling. The composition of the thus constituted feedstock at the inlet of the reactor is described in the table below.

The feedstock is treated at 380° C. and under 8 bar of partial hydrogen pressure. The composition of the recipe at the outlet of the reactor, collected at a catalyst age of 168 hours (recipe 1), is provided in the table below. The paraxylene yield is 13.91%, and the conversion of the ethylbenzene is 39.13%, which corresponds to the initial activity in ethylbenzene conversion.

After 1464 hours of operation, under the same operating conditions, recipe 2 is collected at the outlet of the reactor. 1296 hours of hydrocarbon contact deactivated the catalyst. The paraxylene yield significantly decreased and is equal to 13.59%; the conversion of the ethylbenzene itself significantly decreased and is equal to 33.31%. The catalyst that has left the reactor contains 3.2% by weight of coke. The activity of the catalyst represents 85% of the initial activity of ethylbenzene conversion.

The catalyst is then regenerated in-situ by stages of combustion and oxychlorination. The combustion consists in bringing the catalyst to a temperature of 360° C. under nitrogen, then in gradually introducing oxygen. When the exothermicity exceeds 10° C., the injection of oxygen is stopped until the temperature stabilizes, then resumes. When the temperature is stable under 5% by volume of oxygen relative to the nitrogen-oxygen mixture, the temperature is increased by 20° C. under nitrogen, and the same procedure for adding oxygen is then repeated. The same procedure is performed so as to reach 500° C. at the end of combustion. At the end of combustion, the catalyst is left for 2 hours under air at 500° C., then the temperature is brought back down to the ambient temperature under air.

At the end of the combustion, the coke content is equal to 0.2% by weight, or an elimination of close to 94% of the quantity of coke that is present on the catalyst before the combustion. The dispersion of platinum is equal to 64%.

The oxychlorination that is performed after the combustion consists in raising the temperature of the catalyst under air to 480° C. under a flow rate of 4 l/h/g, then in injecting water and perchloroethylene $C_2Cl_4$ at respective concentrations of 1.5% by weight and 1% by weight for 3 hours. The quantity of injected chlorine during the oxychlorination is thus equal to 2.5% by weight of Cl relative to the catalyst mass.

The dispersion of platinum is equal to 90%.

After regeneration, the same feedstock is isomerized in the reactor under the same operating conditions. The composition of the recipe at the outlet of the reactor, collected at a catalyst age of 168 hours (recipe 3) is provided in the table below. The paraxylene yield is 13.87%, and the conversion of ethylbenzene is 38.89%. Regeneration of the catalyst made it possible to restore the initial catalytic performance levels.

| Compounds | Feedstock (% by Weight) | Recipe 1 (% by Weight) New Catalyst | Recipe 2 (% by Weight) After 1464 Hours of Contact with Hydrocarbons | Recipe 3 (% by Weight After Regeneration |
|---|---|---|---|---|
| C1-C8 Paraffins | 0.36 | 2.26 | 1.59 | 2.15 |
| C5-C9 Naphthenes | 3.55 | 11.84 | 10.15 | 11.9 |
| Benzene | 0.00 | 0.10 | 0.09 | 0.10 |
| Toluene | 0.23 | 0.54 | 0.42 | 0.51 |
| o-Xylene | 18.40 | 17.50 | 18.20 | 17.63 |
| m-Xylene | 59.92 | 40.69 | 42.21 | 40.60 |
| p-Xylene | 4.77 | 18.68 | 18.36 | 18.64 |
| Ethylbenzene | 12.73 | 7.75 | 8.49 | 7.78 |
| AC9+ | 0.04 | 0.64 | 0.49 | 0.69 |

The invention claimed is:

1. A process for regeneration of a catalyst at least one EUO-structural-type zeolite in acid form and at least one hydro-dehydrogenating metal, having been used in a process for isomerization of a hydrocarbon feedstock comprising aromatic compounds with eight carbon atoms, said regeneration process comprising at least:
a) a stage for eliminating a majority of coke deposited on said catalyst, by combustion of the coke in the presence of a gas that contains oxygen at a temperature that is less than or equal to 600° C.,
b) a stage for oxychlorination of the catalyst is obtained from stage a), carried out between 200 and 550° C. in the presence of at least one gas mixture containing at least oxygen, water, and chlorine and/or at least one chlorinated compound.

2. A process according to claim 1, in which the stage for eliminating coke is conducted such that the content by weight of residual coke in the catalyst after combustion is less than 20% of the content by weight of coke of the catalyst before combustion.

3. A process according to claim 1, in which the gas used in stage a) for the combustion of coke contains 0.1 to 20% by volume of oxygen.

4. A process according to claim 1, in which the oxychlorination stage is carried out between 400 and 500° C.

5. A process according to claim 1, wherein the gas in step (b) comprises a chlorinated mineral compound.

6. A process according to claim 1, wherein the gas in step (b) comprises a chlorinated organic compound.

7. A process according to claim 6, in which the chlorinated organic compound comprises a chloroalkane.

8. A process according to claim 1, in which the content by weight of oxygen of said gas mixture used in stage b) is 10 to 50%.

9. A process according to claim 1, in which the quantity of chlorine and/or chlorinated compound used in stage b) represents in all 0.5 to 10% by weight calculated by weight of chlorine relative to the catalyst weight used to carry out stage a).

10. A process according to claim 1, in which the EUO-structural-type zeolite comprises silicon and at least one element T selected from aluminum, iron, gallium or boron, with an overall Si/T atomic ratio that is more than 5.

11. A process according to claim 1, in which the catalyst comprises at least one matrix.

12. A process according to claim 1, in which the hydro-dehydrogenating metal comprises a metal from groups VB, VIB, VIIB, or VIII of the periodic table.

13. A process according to claim 1, in which the hydro-dehydrogenating metal comprises a metal of group VIII.

14. A process according to claim 1, in which the catalyst comprises at least one metal from among the metals of groups IIIA and IVA.

15. A process according to claim 1, further comprising a stage wherein the regenerated catalyst obtained at the end of stage b) is subjected to a reduction.

16. A process according to claim 1, further comprising recycling the resultant regenerated catalyst to said isomerization process.

17. A process according to claim 16, further comprising a stage, in which said regenerated catalyst is subsequently subjected to a sulfurization treatment.

18. A process according to claim 16, further comprising a stage, in which said regenerated catalyst is subsequently subjected to passivation with ammonia.

19. A process according to claim 1, wherein the gas in stage (a) contains 0.1 to 20% by volume of oxygen, the oxychlorination step is conducted at 400-500° C. with a gas comprising a chloroalkane in an amount representing 0.5-10% by weight calculated by weight of chlorine relative to the weight of catalyst used to carry out stage (a) and the amount of oxygen in the gas mixture used in stage (b) is 10 to 50% by weight.

20. A process for regeneration of a catalyst at least one EUO-structural-type zeolite in acid form and at least one hydro-dehydrogenating metal, having been used in a process for isomerization of a hydrocarbon feedstock comprising aromatic compounds with eight carbon atoms, subsequent to pretreatment by oxychlorination, said regeneration process comprising at least:
a) a stage for eliminating a majority of coke deposited on said catalyst, by combustion of the coke in the presence of a gas that contains oxygen at a temperature that is less than or equal to 600° C.,
b) a stage for oxychlorination of the catalyst is obtained from stage a), carried out between 200 and 550° C. in the presence of at least one gas mixture containing at least oxygen, water, and chlorine and/or at least one chlorinated compound.

* * * * *